(12) United States Patent
Franklin et al.

(10) Patent No.: US 7,347,992 B2
(45) Date of Patent: *Mar. 25, 2008

(54) STICK COMPOSITIONS

(75) Inventors: Kevin Ronald Franklin, Wirral (GB); Jason Richard Williams, Wirral (GB)

(73) Assignee: Unilever Home & Personal Care USA division of Conpco, Inc., Chicago, IL (US)

( * ) Notice: Subject to any disclaimer, the term of this patent is extended or adjusted under 35 U.S.C. 154(b) by 745 days.

This patent is subject to a terminal disclaimer.

(21) Appl. No.: 10/842,137

(22) Filed: May 10, 2004

(65) Prior Publication Data

US 2004/0223996 A1   Nov. 11, 2004

(30) Foreign Application Priority Data

May 10, 2003   (GB) ................. 0310771.1

(51) Int. Cl.
*A61Q 15/00* (2006.01)
*A61K 8/02* (2006.01)

(52) U.S. Cl. .................. 424/65; 424/400; 424/401

(58) Field of Classification Search ............... 424/65, 424/400, 401
See application file for complete search history.

(56) References Cited

U.S. PATENT DOCUMENTS

| | | | |
|---|---|---|---|
| 3,969,087 A | 7/1976 | Saito et al. | 44/7 |
| 5,429,816 A | 7/1995 | Hofrichter et al. | 424/66 |
| 5,650,144 A | 7/1997 | Hofrichter et al. | 424/66 |
| 5,840,286 A | 11/1998 | Gardlik et al. | 424/65 |
| 5,840,287 A | 11/1998 | Guskey et al. | 424/65 |
| 6,241,976 B1 | 6/2001 | Esser et al. | 424/65 |
| 6,287,544 B1 | 9/2001 | Franklin et al. | 424/65 |
| 2002/0159961 A1 | 10/2002 | Yamato et al. | 424/65 |

FOREIGN PATENT DOCUMENTS

| | | |
|---|---|---|
| WO | 93/23008 | 11/1993 |
| WO | 03/005977 | 1/2003 |

OTHER PUBLICATIONS

Co-pending application: Applicant: Emslie et al., U.S. Appl. No. 10/842,094, filed May 10, 2004.
Co-pending application: Applicant: Emslie et al., U.S. Appl. No. 10/842,136, filed May 10, 2004.
PCT International Search Report in a PCT application PCT/EP 2004/004507.
GB Search Report in a GB application GB 0310771.1.
PCT International Search Report in a PCT application PCT/EP 2004/004512.
PCT International Search Report in a PCT application PCT/EP 2004/004514.

*Primary Examiner*—Shelley A. Dodson
(74) *Attorney, Agent, or Firm*—Karen E. Klumas

(57) ABSTRACT

Anhydrous cosmetic antiperspirant stick compositions containing a continuous phase of a water-immiscible cosmetic oil structured by a fibre-forming amido structurant can exhibit undesirable sensory properties when 12-hydroxystearic acid is employed as primary gellant and the preparation of sick compositions suffers from sever processing difficulties when certain of such amido structurants are employed as primary gellant. Stick compositions having desirable sensory properties can be made by employing as primary gellant, a combination of amido structurants comprising (i) an N-acylaminoacid amide in which the N-acyl substituent has the formula —CO—$R^x$ in which $R^x$ represents a branched $C_6$ to $C_{11}$ alkyl group and (ii) an N-acylaminoacid amide in which the N-acyl substituent contains a linear alkyl group and the cosmetic carrier oil comprising from 25 to 50% by weight of a water-immiscible monohydric alcohol that is liquid at 20° C. and a boiling point of higher than 100° C.

37 Claims, No Drawings

STICK COMPOSITIONS

The present invention relates to stick compositions and in particular to such compositions containing a suspended antiperspirant or deodorant, and a carrier material therefor comprising a cosmetically acceptable water-immiscible oil that is solidified by an amido-substituted amino acid, and to their preparation and use.

TECHNICAL FIELD BACKGROUND AND PRIOR ART

Cosmetic antiperspirant formulations are known and available to the public in several different physical forms for application using the corresponding type of applicator, including dispensers for powder mixes, foams, gelled or thickened liquids, liquids of low viscosity that can be sprayed, aerosol formulations, creams, soft solids and sticks. The preferred choice of physical form can often depend on the history of product, and local preferences, which may themselves vary over time as fashions change. One physical form which has been popular especially in North America for antiperspirant and deodorant compositions during the last twenty years is that of sticks. The term "stick" herein is employed in its natural meaning, that is to say a material that is firm to the touch, is often in the shape of a rod or bar and commonly is housed in a container comprising a barrel having an open end and an opposed piston which can be slid up the barrel to expel the stick, which retains its shape and integrity during its expulsion.

Cosmetic antiperspirant sticks typically comprise an antiperspirant active that is dissolved or suspended in a cosmetically acceptable carrier material of which at least a fraction is a cosmetically acceptable water-immiscible oil. In one highly desirable class of cosmetic sticks, the carrier material comprises either no polar liquid or no more than the proportion that can form a single liquid phase with the water-immiscible oil or oil mixture.

One class of material that has hitherto been proposed for solidifying water-immiscible oils comprises non-polymeric fibre-forming structurants. A number of such structurants comprise alkyl ester derivatives of certain saccharides, such as maltose or particularly cellobiose, and others comprise N-acyl amido derivatives of aminoacids, di- or tri-carboxylic acids or cyclohexane. The present invention is directed particularly to compositions in which a continuous phase comprising a water-immiscible oil is solidified with N-acyl amido derivatives of aminoacids.

Many N-acyl amido derivatives of aminoacids that are suitable for solidifying cosmetically-acceptable oils to a greater or lesser extent have been described by Ajinomoto Co Ltd in U.S. Pat. No. 3,969,087, including in particular derivatives of glutamic acid or aspartic acid. The derivative disclosed therein that was apparently the most preferred by Ajinomoto was N-lauroylglutamic acid,-di-n-butylamide, as also indicated by the fact that for many years, it was the only such material that was commercially available from them (trade name GP-1).

GP-1 structurant has been disclosed for use or used in structuring water-immiscible oils in cosmetic sticks, but often not by itself and instead in combination with one or more structurants, for example providing the minor weight proportion of the structurant mixture. Thus, for example Hofrichter et al (Procter & Gamble) in U.S. Pat. No. 5,650,144, U.S. Pat. No. 5,591,424 and U.S. Pat. No. 5,429,816 describe the formation of sticks in which a cosmetic oil is solidified with a mixture of a major proportion of 12-hydroxystearic acid or related compounds (primary gellant) and a minor proportion of an N-acyl aminoacid amide (secondary gellant), exemplifying GP-1 and related N-acyl glutamic acid di-amides in a weight proportion to 12-HSA of 2:6. The combination of hydroxystearic acid and N-acyl aminoacid amides gellants described in the Hofrichter patents supra can be processed under acceptable processing conditions, which is a very desirable attribute.

In the course of investigations leading to the instant invention, it was found that although sticks can be made using N-acyl aminoacid amides such as GP-1 as primary or sole gellant, the resultant product was comparatively soft when made, depositing a "wet" oily film on skin when applied topically. Such a feel is disliked by consumers. Such disadvantageous properties tended to become worse during storage of the product.

The comparative softness of such products made using GP-1 has been recognised by Ajinomoto themselves. More recently, in USA-2002/0159961, Ajinomoto has described a selection of N-acyl amido derivatives of aminoacids from within the overall ranges described in U.S. Pat. No. 3,969,087. In this selection, the alkyl group $R^3$ in the N-acyl substituent —CO—$R^3$ is characterised by containing from 7 to 10 carbon atoms, and may be branched. The '961 specification discloses that the new selection of aminoacid derivatives can be employed to gel non-polar organic liquids to produce harder gels. The '961 specification also discloses the formation of antiperspirant compositions gelled by a representative member of their selected gellants alone or mixed with GP-1, but as the minor gellant in combination with hydroxystearic acid as primary gellant (weight ratio of 2:7). Although compositions employing such a combination of gellants can be processed relatively easily to form sticks, the resultant products exhibited unacceptable sensory properties, and deposited comparatively high weights of composition on a substrate.

In considering how to overcome the problem of poor sensory properties and high deposition of the composition, any investigator has also to make allowance for potential manufacturing difficulties when employing certain amido gellants. It becomes increasingly difficult to form stick compositions as the concentration of such gellants increases. The temperature at which a water-immiscible cosmetic oil gels when employing N-acyl aminoacid amide gellant having a branched N-acyl substituent compared with the same amount of a like gellant having a linear N-acyl substituent. For otherwise identical compositions, the gellant having the branched N-acyl substituent causes such a composition to gel at a significantly higher temperature, for example a difference of over 20° C. A mixture of a gellant such as an N-acyl aminoacid amide and a carrier oil needs to be heated to substantially above its gelation temperature before the gellant dissolves, and it is commonly impractical for antiperspirant or deodorant compositions to be heated to amide dissolution temperatures, so that, in practice, it is impractical to redissolve the gellant by heating such a composition once it has gelled and it accordingly remains gelled. Consequently, it is inherently disadvantageous to employ a gellant that gels the composition at a significantly higher temperature, such as to above the boiling point of water. An elevated gelation temperature introduces a substantial risk that the composition would be gelled before it has been cooled to a temperature at which an active constituent or a temperature sensitive constituent can be introduced, or that the very act of introduction of the active constituting a significant proportion of the overall composition would lower the composition temperature rapidly below the oil gelation temperature, rendering subsequent operations extremely difficult if not impossible on a bulk scale, such as filling of product dispensers.

However, the formulator seeks also to take into account the sensory properties of the resultant formulation. In the course of devising the present invention, it has been found that the proportion of water-immiscible alcohol that can be included in the carrier liquid is important in contributing to the sensory properties of the final formulation. In general terms, such properties become impaired as the proportion increases.

SUMMARY OF THE INVENTION

It is an object of the present invention to avoid or at least ameliorate one or more of the difficulties or disadvantages indicated hereinabove in the preparation of solidified water-immiscible oils containing a cosmetic active ingredient.

According to one aspect of the present invention, there is provided a cosmetic antiperspirant or deodorant composition as described hereinafter in claim 1.

By the employment of the combination of fibre-forming structurants as primary gellant in accordance with claim 1 together with the employment of the specified alcohol within the specified window of proportions of the water-immiscible carrier liquid, it is possible to prepare cosmetic sticks in a manner that ameliorates one or more of the problems identified hereinbefore. Desirably, enough water-immiscible alcohol is employed to enable the formulation to be processed, but not so much that the sensory properties of the resultant formulation are excessively impaired.

In the present invention, the selected amido gellants (i) and (ii) together constitute the primary gellant, which is to say that they are employed by themselves or if a secondary gellant is present they together constitute the major weight proportion of the total of primary and secondary gellants.

The invention compositions herein are anhydrous, by which is meant herein that the liquid carrier oils do not contain a polar phase such as a dispersed aqueous phase.

According to a second aspect of the present invention, there is provided a process for the preparation of an cosmetic antiperspirant or deodorant composition as described in claim 33.

According to a third aspect of the present invention there is provided a cosmetic method for inhibiting or controlling perspiration and/or body malodours by the topical application to skin of an effective amount of a composition according to the first aspect.

DETAILED DESCRIPTION OF THE INVENTION AND PREFERRED EMBODIMENTS THEREOF

The present invention relates to antiperspirant or deodorant sticks containing a cosmetic antiperspirant or deodorant active ingredient in which the water-immiscible oil phase is solidified using a mixture of at least two classes of fibre-forming structurants containing an amido linkage of which one class is gellant (i) an N-acyl aminoacid amide, the acyl group containing a branched alkyl group of 4 to 12 carbon atoms. The compositions include at least 4% by weight of amido fibre-forming gellants, of which at least 3% is constituted by the primary gellant, i.e. classes (i) and (ii) together. Herein, the term amido gellants includes cyclodipeptides.

Gellant (i)

Gellant (i) is an N-acyl aminoacid amide that satisfies general formula (1) $A^X$—CO—$R^X$ in which $A^X$ represents the residue of an amino acid amide and $R^X$ represents a branched alkyl group containing from 4 to 12 carbon atoms and sometimes 7 to 10 carbon atoms. In many instances, the aminoacid amide residue $A^X$ can be represented by formula (2)

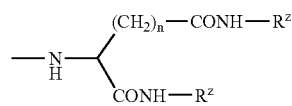

in which n represents an integer of 1 or 2 and $R^Z$ represents an alkyl group, which can be linear or branched, containing from 1 to 10 and particularly from 3 to 5 carbon atoms, each of which $R^Z$ groups can be the same or different. Accordingly, such an amino acid from which the amide residue $A^X$ is derivable is glutamic or aspartic acid. In some especially preferred embodiments, each $R^Z$ represents a butyl group, especially an n-butyl group, and particularly in the derivative of glutamic acid, which residue is represented by formula (3)

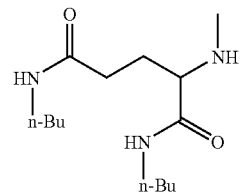

In formula (1), $R^X$ preferably represents an alkyl group containing either one or two or possibly three side chains, such as particularly one side chain. Desirably, any side chain in $R^X$ contains from 1 to 4 carbon atoms, such as methyl, ethyl propyl or butyl, and often from 1 to 3 carbon atoms, of which ethyl is very convenient. The alkyl backbone preferably contains from 4 to 8 carbon atoms, often from 4 to 7 carbon atoms and sometimes 7 or 8 carbon atoms. The location of the side chain along the alkyl group backbone is at the discretion of the producer, of which the 2 position is often favoured. An especially desirable branched chain group for $R^X$ is 1-ethylpentyl, so that the resultant acyl group is 2-ethylhexanoyl. Other branched chain groups for $R^X$ include 1-methylbutyl, isobutyl and 1-butylheptyl. It is particularly desirable to employ a gellant (i) in which $R^X$ is according to one or more of the branched alkyl groups named above and the amide residue is derived from glutamic acid dibutylamide.

The weight proportion of gellant (i) in the composition is commonly selected in the range of at least 1.5% w/w, in many desirable embodiments is up to 8% and particularly at least 2% w/w. It is often unnecessary to employ more than 6% w/w of gellant (i) in the composition. The proportion of gellant in the composition can also be determined by relation to the water-immiscible phase which it is structuring, i.e excluding the weight of any material which is suspended in the carrier oils constituting that phase. The weight proportion of gellant (i) is usually selected in the range of from 3 to 15% w/w of the water-immiscible phase and is often present in a proportion of at least 4% w/w of that phase. Its weight proportion of that phase in a number of preferred embodiments is up to 9%. The weight proportion of each gellant in the composition or water-immiscible phase will often be selected in concert with the proportion of co-gellant (ii) the choice and weight of any secondary gellants, and the desired hardness of the stick.

Gellant (i) is employed in conjunction with a second amide-fibre-forming structurant, (ii), that is an N-acyl aminoacid amide other than the branched-chain substituted N-acyl aminoacid amides of gellant (i).

N-acyl aminoacid amides according to gellant (ii) are described in U.S. Pat. No. 3,969,087. A list of many of such amides and the general method of manufacture are described in said patent specification in column 1 line 63 to column 4 line 47, and specific amido derivatives are named in Example 1 in column 6 to 8, which passages from the text are incorporated herein by reference. Herein, gellant (11a) often satisfies formula (4) $A^Y$-CO—$R^Y$ in which $A^Y$ represents an amino acid amide and $R^Y$ represents a linear alkyl group containing from 9 to 21 carbon atoms. Highly desirably, $A^Y$ represents an amino acid amide residue in accordance with the formula (5)

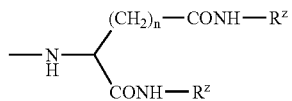

in which n represents an integer of 1 or 2 and $R^Z$ represents an alkyl group, which can be linear or branched, containing from 1 to 10 and particularly from 3 to 5 carbon atoms, each of which $R^Z$ groups can be the same or different. Accordingly, the amino acid from which such an amide residue is derivable is glutamic or aspartic acid. In some especially preferred embodiments, each $R^Z$ represents a butyl group, especially an n-butyl group, and particularly in the derivative of glutamic acid. Such a is represented by formula (3), given supra for residue $A^X$.

In formula (5), $R^Y$ often contains from 9 to 15 linear carbons, of which one preferred group comprises undecyl.

N-Lauroyl-L-glutamic acid di-n-butylamide, formula (6)

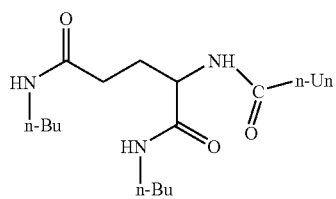

(n-Un=undecyl) employed in Example 14 of '087, is an especially desirable amide structurant for employment in the instant invention compositions and is commercially available from Ajinomoto under their trade designation GP-1.

Herein, the weight proportion of gellant (ii) in the composition is commonly selected in the range of at least 1.5% w/w and in many desirable embodiments is up to 8% and particularly at least 2% w/w. It is often unnecessary to employ more than 6% w/w of gellant (ii) in the composition. The proportion of gellant (ii) in the composition can also be determined by relation to the water-immiscible phase which it is structuring. The weight proportion of gellant (ii) is usually selected in the range of from 3 to 12% w/w of the water-immiscible phase and is often present in a proportion of at least 3.5% w/w of that phase. Its weight proportion of that phase in a number of preferred embodiments is up to 8%. The weight proportion of the gellant in the composition or water-immiscible phase will often be selected in concert with the choice and proportion of any secondary gellant or gellants, and the desired hardness of the stick.

The weight ratio of gellant (i) to gellant (ii) is often selected in the range of from 3:1 to 1:3. In many instances the weight ratio is no higher than 2:1 and in such or other instances, the weight ratio is at least 1:2. A convenient weight ratio can be in the range of 1.1:1 to 1:1.1.

The combined weight proportion of gellants (i) and (ii) in the composition is often selected in the range of from 4 to 10% and in some well desired embodiments from 4.5 to 8%, particularly at least 5%. When expressed in terms of the weight proportion of the two gellants in the water-immiscible phase, this is often from 6 to 15% w/w of the phase and in many desirable embodiments from 7.5 to 12% w/w.

The primary gellant combination can be employed by itself, or if desired can be supplemented by a secondary gellant, i.e. a gellant or gellants other than gellants (i) and (ii). Secondary herein indicates that such a gellant or gellants constitute the minor fraction of the total weight of gellants in the composition, and preferably not more than a third of the total weight of gellants. The primary gellants, i.e. the combination of gellants (i) and (ii) always contribute at least 3% and often at least 3.5% by weight of the composition. In many desirable embodiments the proportion of secondary gellants is from 0 to 25% w/w of the total weight of gellants. Conveniently, the composition can be free or nearly free from secondary gellants, such as containing from 0 to 5% w/w of the gellants (based on the weight of the composition).

The secondary gellants can, desirably, be selected from gellant (iii) namely fibre-forming amide derivatives of carboxylic acids other than amino acid amides of gellants (i) and (ii) or from gellant (iv) namely hydroxystearic acids. The combined weight proportion of gellants (i), (ii) and (iii) is at least 4% of the composition.

Such other amide derivatives (iii) can conveniently be selected from, (iiia) diamido or triamido substituted cyclohexane, gellant (iiib), amide derivatives of di and tribasic carboxylic acids (iiic) hydroxystearic acid amides, and (iiid) cyclodipeptides. It is often convenient to select amide gellant (iii) from sub-classes (iiia) to (iiic).

Secondary gellants, (iiia) comprise di-amido and triamido-substituted cyclohexane. Particular sub-classes of such compounds comprise –1,2 or –1,3 substituted cyclohexane compounds, and 1,3,5-triamido-substituted cyclohexane in which the amido group desirably accords with the general formula —$(CH_2)_v$—CO—NH—$R^{111}$ and —$(CH_2)_v$—NH—CO—$R^{111}$) in which $R^{111}$ represents an alkyl group of from 5 to 27 carbon atoms and v is an integer selected from zero and one.

When the cyclohexane ring is substituted by two amido substituents, the substituents preferably satisfy —$(CH_2)_v$—NH—CO—$R^{111}$) and are very desirably in the 1,2 or 1,3 positions relative to each other around the cyclohexane nucleus. When they are in the 1,3 relative positions, v preferably represents 1. When the two substituents are in the 1,2 relative position, v preferably is zero.

When the cyclohexane ring is substituted by three amido groups, they each preferably satisfy —(CH$_2$)$_v$—CO—NH—R$^{111}$. R$^{111}$ can be linear or branched. Preferably the number of carbons in R$^{111}$ is selected in the range of 8 to 20. For example undecyl, dodecyl, octadecyl, or dimetyloctyl.

Secondary gellant (iiib) comprises amide derivatives of di and tribasic carboxylic acids. Such gellants are in accordance with the description either as set forth in U.S. Pat. No. 5,840,288 and specifically the passage from column 12 line 37 to column 14 line 20 or as set forth in U.S. Pat. No. 6,190,673B1, specifically the passages col 1 line 47 to col 2 line 38 and col 3 line 47 to col 5 line 23. Their general methods of manufacture are as described in the passage in U.S. Pat. No. 5,840,288 in column 12 line 37 to 39 or as set forth in U.S. Pat. No. 6,190,673B1, in the passage in col 5 lines 28 to 43. Convenient carboxylic acid for the preparation of amide derivatives include succinic acid and aliphatic acids containing three vicinal carboxylic acid groups such as 1-propene-trioic acid. Each amide substituent preferably contains an alkyl, especially linear alkyl group of from 3 to 12 carbons. Specific suitable gellants (iiib) are listed in column 13 line 62 to column 14 line 7 in U.S. Pat. No. 5,840,288 and in Table 1 in col 13 of U.S. Pat. No. 6,190,673B1. A particularly preferred gellant (iiib) is 2-dodecyl-N,N'-dibutylsuccinimde or 1-propene-1,2,3-trioctylamide or 2-hydroxy-1,2,3-propane-tributylamide. Such passages are incorporated herein by reference.

Secondary gellant (iiic) of amido gellants within gellant (iii) comprises hydroxystearamides and in particular 12-hydroxy-stearamides. The amido substituent in such amides preferably contains an alkyl, particularly a linear alkyl group between 3 and 13 carbon atoms, such as propyl, butyl, heptyl or undecanyl.

Secondary gellants (iiid) suitable for employment in the instant invention comprises structurants which satisfy the following general formula:—

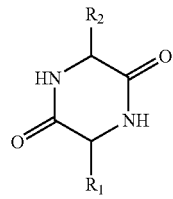

in which one of R$_1$ and R$_2$ represents an alkyl, alkyl ester group and the other represents an alkyl or alkaryl group. Examples of such amides are described in two papers by Hanabusa et al, entitled respectively Cyclo(dipeptide)s as low molecular-mass Gelling Agents to harden Organic Fluids, J. Chem Soc. Commun., 1994 pp1401/2, and Low Molecular Weight Gelators for Organic Fluids: Gelation using a Family of Cyclo(dipeptide)s, in the Journal of Colloid and Interface Science 224, 231-244 (2000), which descriptions of amide structurants are incorporated herein by reference.

However, it is especially preferred to employ herein a sub-class of cyclodipeptides not expressly disclosed by Hanabusa, which sub-class satisfies the general formula:—

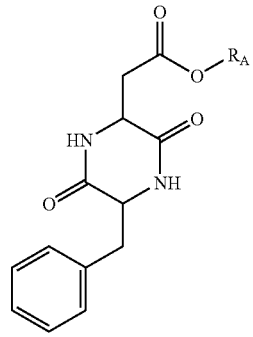

in which R$_A$ represents a carbocyclic or heterocyclic group containing not more than 2 rings. Such materials are sometimes herein referred to as DOPA derivatives.

In DOPA derivatives, R$_A$ can comprise two fused rings, but preferably comprises a single six membered ring, either carbocyclic or heterocyclic, or a bridged ring. When A is carbocyclic, it can be either saturated or unsaturated, preferably unsaturated or aromatic. When R$_A$ is heterocyclic, it is preferably saturated.

Although the cyclic group within R$_A$ can be unsubstituted, it is preferably substituted by at least one alkyl substituent, which preferably contains no more that 16 carbon atoms. In some highly desirable embodiments the alkyl substituent has a longest chain length of up to 4 carbon atoms, and in certain or those a total carbon content of up to 5 carbon atoms. The alkyl substituent may be linear or branched. Preferred examples include methyl, ethyl, propyl, isopropyl, butyl isobutyl or t-butyl or isopentyl. In a number of very suitable DOPA derivatives, R$_A$ contains two or more alkyl substituents and especially those selected from the above list of preferred examples. The alkyl substituents may be the same, such as two or more methyl substituents, or may be a combination of different substituents such as a methyl and isopropyl substituents. When R$_A$ is saturated, the substituents may depend from the same carbon atom in the ring, such as two methyl groups, or from different carbon atoms. In several highly desirable derivatives, two alkyl substituents are meta or para to each other, for example meta methyl groups or a para methyl and isopropyl group. In yet other derivatives, the ring may include a methylene bridge, which preferably likewise completes a six membered ring.

In some suitable DOPA derivatives, the or one alkyl substituent may be ortho or para to the bond with the DOPA residue, as in 4-methyl-phenyl-. In some or other DOPA derivatives, the bond with the DOPA residue is meta to one or preferably two methyl substituents.

When R$_A$ is heterocyclic, the heterocyclic atom is suitably nitrogen. Conveniently, the heterocyclic atom can be para to the bond with the DOPA residue. Moreover, in a number of desirable derivatives, the heteroatom is ortho to at least one alkyl group, better in a saturated ring and especially to up to 4 ortho methyl groups.

The group R$_A$ is often most easily referred to as the residue from the corresponding alcohol which may be reacted with DOPA to form the ester linkage. Thus, desirable examples of R$_A$ include the residues from 4-alkyl phenol, such as 4-nonyl-phenol, and 2,6-dialkyl- or 2,2,6,6-tetraalkyl-4-piperidinol, such as 2,2,6,6-tetramethyl-4-piperidinol.

In some preferred DOPA derivatives, the ring in $R_A$ is carbocyclic, and is substituted by at least two alkyl groups of which at least one is methyl and the other or one of the others is isopropyl. Examples of such preferred $R_A$ residues include menthol, isopinocamphenol and 3,5-dialkyl cyclohexanol such as 3,5-dimethyl cyclohexanol. Especially preferred $R_A$ residues include thymol. Yet others include the DOPA derivatives from carveol and carvacrol.

The DOPA derivatives used in this invention may be a mixture of compounds within the general formulae given, or may be a single compound.

The DOPA derivatives can be prepared by reacting the respective alcohol with DOPA in acid form (DOPAA), or possibly with an acid chloride, or possibly an anhydride or an ester containing a DOPA residue. DOPAA can be obtained by cyclising aspartame. DOPAA can be reacted with the relevant alcohol of formula $R_AOH$, preferably in a mole ratio to the DOPAA of at least 2:1 in dimethyl sulphoxide, in a ratio of from 6:1 to 12:1, in the presence of a promoter, such as a carbonyldiimidazole, in an amount preferably from 0.5 to 2 moles of promoter per mole of DOPA acid. The reaction is conveniently carried out at a temperature from 40 to 60° C.

Secondary gellant (iv) is a hydroxystearic acid, and more desirably 12-hydroxystearic acid.

Secondary gellants (iii) and (iv) can be employed without each other or together with each other, for example in a weight ratio of 3:1 to 1:3.

Herein, the total weight proportion of the secondary gellants (iiia) to (iiid) and (iv) in the composition is commonly selected in the range of 0 to 5% and in many desirable embodiments is not more than 3% w/w, recognising that the weight still constitutes a minor proportion of the total weight of gellants. The proportion of the secondary gellant (iiia) to (iiid) and (iv) in the composition can also be determined by relation to the water-immiscible oils which it is structuring. The weight proportion of said secondary gellant is usually selected in the range of from 0 to 7.5% w/w of the water-immiscible oils and is often present in a proportion of not more than 4.5%% w/w of those oils. The weight ratio of gellant (iii) to gellant (iv), if both are present, can conveniently be selected in the range of from 3:1 to 1:5.

The combined weight proportion of primary and secondary gellants in the composition is often selected in the range of from 4 to 10% and in some well desired embodiments from 5 to 8%. When expressed in terms of the weight proportion of the two gellants in the water-immiscible oils, this is often from 6 to 15% w/w of the oils and in many desirable embodiments from 7.5 to 12% w/w.

Water-Immiscible Carrier Oils

Aliphatic alcohols which are liquid at 20° C. are employed herein within the proportion of from 25 to 50% w/w of the carrier oils. Especially desirably such materials are water-immiscible. These include branched chain alcohols of at least 10 carbon atoms and in many instances up to 30 carbon atoms, particularly 15 to 25, such as isostearyl alcohol, hexyl-decanol octyl-dodecanol and decyl-tetradecanol. Other suitable water-immiscible alcohols include intermediate chain length linear alcohols, commonly containing from 9 to 13 carbon atoms, such as decanol or dodecanol. A further suitable alcohol is benzyl alcohol. Such alcohols can assist in the process of forming a solution of the amido-substituted gellants (i), (ii) and (iii), if present, in a water-immiscible carrier liquid during the manufacture of structured gels. Such alcohols can often constitute from at least 30% to 45% by weight of the oils. In a number of compositions, the proportion is from 35 to 40% by weight of the oils. In addition to controlling the total proportion of monohydric alcohol that is present in the water-immiscible oils, it is highly desirable to select its content in relation to the total weight of amide gellants (i), (ii) and any (iii). The weight ratio of such monohydric alcohol to the combined weight of amido gellants is preferably from 3.5:1 to 5:1.

Aliphatic alcohols which are solid at 20° C., e.g. linear alcohols containing at least 12 carbons, such as stearyl alcohol can also be contemplated as secondary structurants, but they are preferably absent or present in no more than 3% by weight of the whole composition, as indicated hereinbefore, since they lead to or increase visible white deposits when a composition structured by them is topically applied to skin.

The water-immiscible carrier liquid comprises one or a mixture of materials which are relatively hydrophobic so as to be immiscible in water. Following partition between the continuous phase and the disperse phase, a small fraction of hydrophilic liquid may remain in the continuous phase, provided the overall carrier liquid mixture is immiscible with water. It will generally be desired that the carrier oils mixture is liquid (in the absence of structurant) at temperatures of 15° C. and above. It may have some volatility but its vapour pressure will generally be less than 4 kPa (30 mmHg) at 25° C. so that the material can be referred to as an oil or mixture of oils. More specifically, it is desirable that at least 80% by weight of the hydrophobic carrier liquid should consist of materials with a vapour pressure not over this value of 4 kPa at 25° C.

It is preferred that the hydrophobic carrier material includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207™ and Silicone 7158™ from Union Carbide Corporation; and SF1202™ from General Electric.

The hydrophobic carrier employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include products available under the trademarks Dow Corning 556 and Dow Corning 200 series. Other non volatile silicone oils include that bearing the trademark DC704. Incorporation of at least some non-volatile silicone oil having a high refractive index such as of above 1.5, eg at least 10% by weight (preferably at least 25% to 100% and particularly from 40 to 80%) of the silicone oils can be beneficial in some compositions.

Liquid silicone oils can constitute the balance of the water-immiscible liquid carrier oils, ie 50 to 75% w/w of the oil, if desired. However, silicone oils may be supplemented, if desired, buy other oils, and in such instances, there is preferably, sufficient liquid silicone to provide at least 10%, better at least 15%, by weight of the whole composition.

Silicon-free hydrophobic liquids can be used, preferably in addition to liquid silicones. Silicon-free hydrophobic organic liquids which can be incorporated include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms. Hydrocarbon liquids preferably are present in a range of from 0 to 20% w/w and especially from 0 to 5% of the oils.

Other suitable hydrophobic carriers comprise liquid aliphatic or aromatic esters. Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates. Examples of such esters include suitable $C_8$ to $C_{18}$ alkyl benzoates or mixtures thereof, including in particular $C_{12}$ to $C_{15}$ alkyl benzoates eg those available under the trademark Finsolv. Ester oils, be they aliphatic or aromatic desirably comprise from 0 20% and preferably 0 to 10% w/w of the oils.

Further instances of suitable hydrophobic carriers comprise liquid aliphatic ethers derived from at least one fatty alcohol, such as myristyl ether derivatives e.g. PPG-3 myristyl ether or lower alkyl ethers of polygylcols such as an ether having named as PPG-14 butyl ether by the CTFA. Such ethers desirably constitute from 0 to 20, and preferably from 0 to 10% w/w of the oils.

Antiperspirant or Deodorant Actives

The composition preferably contains an antiperspirant active. Antiperspirant actives, are preferably incorporated in an amount of from 0.5-60%, particularly from 5 to 30% or 40% and especially from 5 or 10% to 30 or 35% of the weight of the composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates and activated aluminium chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z.wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)$ COOH.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

The particle size of the antiperspirant salts often falls within the range of 0.1 to 200 μm and particularly from 0.2 to 100 μm, some desirable products having at least 95% by weight of below 50 μm with a mean particle size often from 3 to 30 μm and in many instances from 5 to 20 μm. The weight of particulate active antiperspirant salt herein commonly includes any water of hydration present.

Deodorant Actives

Suitable deodorant actives can comprise deodorant effective concentrations of antiperspirant metal salts, deoperfumes, and/or microbicides, including particularly bactericides, such as chlorinated aromatics, including biguanide derivatives, of which materials known as Igasan DP300™ (triclosan), Tricloban™, and Chlorhexidine warrant specific mention. A yet another class comprises biguanide salts such as are available under the trade mark Cosmocil™. Deodorant actives are commonly employed at a concentration of from 0.1 to 25% by weight.

Optional Ingredients

Optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

The compositions herein can incorporate one or more cosmetic adjuncts conventionally contemplatable for cosmetic solids or soft solids. Such cosmetic adjuncts can include skin feel improvers, such as talc or finely divided polyethylene, for example in an amount of up to about 10%; a moisturiser, such as glycerol, for example in an amount of up to about 5%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

Suspension sticks made with the combination of gellants 9 (i) and (ii) tend to exhibit low visible deposits, compared for example with traditionally wax structured anhydrous compositions and have a good skin feel.

Composition Preparation

A convenient process sequence for preparing a composition according to the present invention comprises first forming a solution of the structurant combination in the water-immiscible liquid or one of the water-immiscible liquids. This is normally carried out by agitating the mixture at a temperature sufficiently high that all the structurants dissolve (the dissolution temperature) such as a temperature in a range from 70 to 140° C. Any oil-soluble cosmetic adjunct can be introduced into oil phase, either before or after the introduction of the structurants. Commonly the resultant structurant solution is allowed to cool to a temperature that is intermediate between that at which the structurants dissolved and the temperature at which it would set, often reaching a temperature in the region of 60 to 90° C.

In some routes, the carrier oils can be mixed together prior to introduction of the gellants and the antiperspirant or deodorant active. In other preparative routes, it is desirable to dissolve all or a fraction of the amide-substituted structurants in a first fraction of the composition, such as a branched aliphatic alcohol, eg isostearyl alcohol or octyl-dodecanol, optionally in conjunction with an alcohol having some water-miscibility and boiling point above the dissolution temperature of the amido gellant in the alcoholic fluid. This enables the remainder of the carrier fluids to avoid being heated to the temperature at which the structurants dissolve or melt. The proportion of the carrier fluids for dissolving the structurants is often from 25 to 50% by weight of the carrier fluids.

In said other preparative routes the particulate material is introduced into preferably a second fraction of the carrier oils, for example silicone and/or ester and/or hydrocarbon oils and thereafter, and thereafter the first fraction containing dissolved structurant and second fraction containing suspended particulate material are mixed at a temperature above that at which the composition gels, and often from 5° C. to 30° C. above the regular setting temperature of the composition, dispensing containers are filled and cooled or allowed to cool to ambient temperature. Cooling may be brought about by nothing more than allowing the container and contents to cool. Cooling may be assisted by blowing ambient or even refrigerated air over the containers and their contents.

Product Dispenser

Suspension sticks according to the present invention are normally housed in dispensing containers, the shape and size of which, the materials of their construction and the mechanisms employed therein for dispensing the antiperspirant sticks are those commensurate with the cosmetic. An antiperspirant or deodorant stick is often housed in a barrel, commonly of circular or elliptical transverse cross section, having an open end through which the stick can pass and an opposed closed end, commonly comprising a platform or elevator that is axially moveable along the barrel. The platform can be raised by the insertion of a finger or more commonly by rotation of an externally exposed rotor wheel that rotates a threaded spindle extending axially through a co-operating threaded bore in the platform. The barrel normally also has a removable cap that can fit over its open end. The barrel is normally made from an extrudable thermoplastic such as polypropylene or polyethylene.

The present invention also provides translucent cosmetic antiperspirant or deodorant products comprising an invention cosmetic stick as described hereinbebefore disposed within a dispensing barrel.

Having summarised compositions according to the present invention and described preferred embodiments, specific embodiments thereof will now be described in more detail by way of example only.

The following constituents were employed in exemplified and comparison suspension sticks hereinafter.

| Ref | CTFA or IUPAC name | Trade name and/or supplier |
|---|---|---|
| C1 | Cyclomethicone | DC245, Dow Corning |
| C2 | 2-hexyl-decanol | Eutanol G16, Cognis |
| C3 | Octyl dodecanol | Eutanol G, Cognis |
| C4 | $C_{12-15}$ alkyl benzoate | Finsolv TN: (Finetex |
| C5 | PPG-14 Butyl Ether | Fluid AP: (Amercol |
| C6 | Sunflower Seed Oil | Alembic |
| G1 | N-(2-ethyl hexanoyl)-L-glutamic acid di-n-butylamide | GA-01, Ajinomoto |
| G2 | N-lauroyl-L-glutamic acid di-n-butylamide | GP-1, Ajinomoto |
| G3 | 12-hydroxystearic acid | 12-HSA, CasChem |
| G4 | N N'-bis (dodecanoyl)-1,2-diaminocyclohexane (non optically active cis/trans mixture). | Preparation as in US 6410003 |
| G5 | N N'-bis (2-ethylhexanoyl)-1,2-diaminocyclohexane (non optically active cis/trans mixture) | Preparation as in US 6410003 |
| G6 | 2-octadecyl-N,N'-dibutylsuccinamide | Preparation as in US 5840287 |
| G7 | n-propyl-12-hydroxystearamide | standard preparation |
| G8 | 2-ethyl butanoyl-L-glutamic acid di-n-butylamide | Preparation hereinbelow |
| S1 | Al/Zr tetraachlorohydrex glycine complex | Reach 908, Reheis |
| S2 | Al/Zr tetraachlorohydrex glycine complex | Westchlor ZR 30BDM CP5, Westwood |
| S3 | Al/Zr Tetrachlorohydrex glycine complex | Rezal 36 GP: Reheis |
| S4 | Fumed Silica | Aerosil 200: Degussa |
| F | Fragrance | |

Measurements of payoff of the stick and visible deposits (whiteness) in the Examples and Comparisons were made on black cotton, 24 hours after application of the stick.

The Example and Comparison sticks were made by the following technique. The carrier oils, C1 and C2 or C3 were mixed together and all the gellants were introduced with stirring. The temperature of the mixture was increased until the gellants dissolved. The resultant gellants solution was allowed to cool to 90° C., and the particulate antiperspirant was introduced. The temperature of the resultant mixture was kept constant at 85° C., and it was stirred thoroughly and any fragrance was then added. The mixture was allowed to cool and then poured into stick barrels at the temperature stated below which was about 5° C. above the regular solidification temperature of the mixture (obtained by allowing a sample to solidify under quiescent conditions, or from previous trials), and allowed to cool to ambient.

The formulations expressed in parts by weight and the properties of the sticks are summarised in Table 1 below.

TABLE 1

|  | Ex 1.1 | Comp 1.A | Comp 1.B | Comp 1.C |
|---|---|---|---|---|
| C1 | 43 | 48 | 43 | 43 |
| C2 | 24.5 |  | 24.5 | 24.5 |
| C3 |  | 14 |  |  |
| G1 | 3.25 | 1 | 1 | 6.5 |
| G2 | 3.25 | 1 | 1 |  |
| G3 |  | 7 | 7 |  |
| S1 | 25 |  | 25 | 25 |
| S2 |  | 26 |  |  |
| F1 | 1 |  | 1 | 1 |
| Processing Conditions | | | | |
| Stick Pour Temp (° C.) | 78 | 55 | 45 | no stick |
| Stick Properties | | | | |
| Hardness (mm) | 10.2 | 18.7 | 29.5 | no stick |
| pay-off (g) | 0.563 | 0.74 | 1.37 | no stick |
| whiteness | 40.8 | 39.8 | 21.9 | no stick |

The stick produced in Ex1.1 was suitably hard with acceptable pay-off, having good skin sensory properties, and only low white/greasy deposits on skin.

The stick produced in comparison Comp 1.A was that of Example 11 in US2002/0159961, employing as primary gellant 12-HSA. The stick exhibited inferior hardness, even though it employed more gellant in total, a higher pay-off, and inferior sensory properties on skin application—a thick, white and greasy deposit, when applied to the skin.

The stick produced in comparison Comp 1.C employed the same carrier oils as in Example 1.1. It was even softer than Comp 1.B, with a substantially greater pay-off and even worse sensory properties—the stick collapsed and left a very thick, white and greasy deposit when applied to skin.

No stick could be produced in Comp 1.C, because the gelation temperature of the solution of oils is significantly above 100° C., ie well above the temperature at which the antiperspirant active could safely be introduced.

Examples 2.1 to 2.4

These Examples were made by the general method employed for Example 1, additionally containing a secondary gellant in class (iii). The formulations expressed in parts by weight and the properties of the sticks are summarised in Table 2 below.

TABLE 2

|  | Ex 2.1 | Ex 2.2 | Ex 2.3 | Ex 2.4 |
|---|---|---|---|---|
| G1 | 2.5 | 2.5 | 2.875 | 2.5 |
| G2 | 2.5 | 2.5 | 2.875 | 1 |
| G4 | 1 |  |  |  |
| G5 |  | 1 |  |  |
| G6 |  |  |  | 2.5 |
| G7 |  |  | 0.25 |  |
| C2 | 24.75 | 24.75 | 24.75 | 24.75 |
| C1 | 43.25 | 43.25 | 43.25 | 43.25 |
| S3 | 25 | 25 | 25 | 25 |
| F | 1 | 1 | 1 | 1 |
| Properties | | | | |
| Stick Pour Temp (° C.) | 68 | 70 | 70 | 70 |
| Hardness (mm) | 11.3 | 11.0 | 9.9 | 11.4 |
| pay-off (black cotton) (g) | 0.595 | 0.598 | 0.614 | 0.625 |

The sticks made in each of Examples 2.1, 2.2, 2.3 and 2.4 were firm opaque sticks. They applied well to skin leaving virtually no white deposits and virtually no oily film.

Examples 3.1 to 3.7

In these Examples, further sticks were made employing other carrier oils and additionally containing a suspended inorganic material, by the general method of Example 1. The formulations, expressed as parts by weight, and the properties of the sticks are summarised in Table 3 below.

|  | Ex 3.1 | Ex 3.2 | Ex 3.3 | Ex 3.4 | Ex 3.5 | Ex 3.6 | Ex 3.7 |
|---|---|---|---|---|---|---|---|
| G1 | 2.75 | 3.25 | 2.75 | 2.5 | 2.5 | 2.5 | 2.5 |
| G2 | 2.75 | 3.25 | 2.75 | 2.5 | 2.5 | 2.5 | 2.5 |
| C4 |  | 11 |  |  |  |  |  |
| C5 |  |  | 17.5 |  | 2.5 |  |  |
| C2 | 20.7 | 24.5 | 20.7 | 20.5 | 18.5 | 18.5 | 27.8 |
| C1 | 47.8 | 32 | 30.3 | 45.5 | 48 | 49.3 | 40.0 |
| S4 |  |  |  | 2 |  | 1 | 1 |
| C6 |  |  |  |  | 1 |  |  |
| S1) | 25 | 25 | 25 | 25 | 25 | 25 | 25 |
| F | 1 | 1 | 1 | 1 | 1 | 1.2 | 1.2 |
| Properties | | | | | | | |
| Stick Pour Temp (° C.) | <90 | 80 | <90 | <90 | <90 | 83 | 68 |
| Hardness (mm) | 11.6 | 10.8 | 11.7 | 9.9 | 12.2 | 11.5 | 11.7 |
| pay-off (black cotton) (g) | n/d | 0.505 | n/d | n/d | n/d | n/d | n/d | n/d indicates that the measurement was not made.

Examples 3.1, 3.6 and 3.7 were evaluated with regard to stability to melting at elevated temperature. All were stable to at least 55° C., showing no irreversible loss of hardness or solvent leakage. This is a big advantage over conventional opaque sticks that are structured using stearyl alcohol as the predominant structurant, possibly with a minor fraction (1 to 5% w/w) of Castorwax. Such sticks have a tendency to soften and lose their structure when the storage temperature reaches or exceeds 50° C. This temperature can be attained in tropical or subtropical climates in warehouses or in transporting wagons unless expensive cooling is carried out.

Example 4

This Example employs an alternative representative of a gellant of class (i), G8. The stick is made by the general method of Example 1. Its composition, expressed in parts by weight, and its properties are summarised in Table 4 below.

Preparative Method for Gellant G8

Gellant G8 was made by a two stage method. In stage 1 the N-acyl L glutamic acid dimethyl ester was formed and in stage 2, this was converted to the corresponding N-acyl L glutamic acid dibutlyamide, both stages employing laboratory grade chemicals from Sigma Aldrich.

A 250 ml 3 necked round bottomed flask equipped with a magnetic stirrer was charged with L-Glutamic acid dimethyl ester hydrochloride salt (15 g, 71 mmol). Dichloromethane (150 ml, approximately 10 mls per gram of the HCl salt) was then introduced to the flask at laboratory ambient temperature (20° C.) with stirring.

Triethylamine (TEA, 8.61 g, 85 mmol) was then added with stirring, whereupon a white precipitate immediately appeared. This mixture was left to stir at room temperature for a period of 60 minutes. A second portion of TEA (7.17 g, 71 mmol) was then added to the reaction mixture together with 2-ethylbutanoic acid chloride (71 mmol in 50 ml DCM) whilst maintaining the temperature between 0° C.-10° C. during the addition. The reaction mixture was stirred overnight at ambient temperature. Next morning, the precipitate was filtered off and a clear filtrate was obtained which was washed successively with dilute hydrochloric acid, saturated sodium bicarbonate solution and water in a separating funnel. Evaporation of all solvent under reduced pressure yielded the corresponding N-Acyl L-Glutamic acid dimethyl ester which was detected to be free from residual acid and starting materials.

In the second stage, the product of stage 1 (typically 10 g, 23-38 mmol) was dissolved in toluene (100 ml, 10 mls per gram of dimethyl ester) then added to a 250 ml reactor vessel equipped with magnetic stirrer, dropping funnel and water condenser. Butylamine in excess (30-50 ml, 300-500 mmol) was then introduced slowly dropwise, after which the reaction solution was heated up to 90° C. and stirred thoroughly. Progress of the conversion from dimethyl ester to diamide was monitored using both RP HPLC and FT-IR on withdrawn samples until no ester was detected any longer or if some ester remained, until the relative intensity of the ester versus the amide infra-red peaks had become constant. The reaction took approximately 24 hours.

When cooled to ambient temperature, the reaction mixture formed a gel which was filtered under vacuum and washed with cold solvent until a crude white solid material was obtained. Residual butylamine was removed by washing the crude product with 25 g acid based Amberlyst A-15™ resin in ethanol, followed by filtration through charcoal to remove colour as per Table 5. Its purity (Area %) was 94.06 and its melting point was 172° C.

TABLE 4

|  | Ex4 |
|---|---|
| G8 | 2.75 |
| G2 | 2.75 |
| C1 | 49.0 |
| C2 | 18.5 |
| S4 | 1.0 |
| S1 | 25.0 |
| F |  |
| Properties |  |
| Hardness (mm penetrometer) | 11.7 |
| Pour Temp ° C. | 90 |

Example 4 had excellent application glide onto skin and left virtually no white deposits.

Measurement of Properties i) Stick hardness—Penetrometer

The hardness and rigidity of a composition which is a firm solid can be determined by penetrometry. If the composition is a softer solid, this will be observed as a substantial lack of any resistance to the penetrometer probe.

A suitable procedure is to utilises a lab plant PNT penetrometer equipped with a Seta wax needle (weight 2.5 grams) which has a cone angle at the point of the needle specified to be 9°10'+/−15". A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted. Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Deposition by Firm Sticks (Pay-Off)

A second property of a composition is the amount of it which is delivered onto a surface when the composition is drawn across that surface (representing the application of a stick product to human skin), sometimes called the pay-off. To carry out this test of deposition when the composition is a firm stick, able to sustain its own shape, a sample of the composition with standardised shape and size is fitted to apparatus which draws the sample across a test surface under standardised conditions of temperature and applied pressure a specified number of times (thrice each way). The amount transferred to the surface is determined as an increase in the weight of the substrate to which it is applied. If desired the colour, opacity or clarity of the deposit may subsequently be determined. A specific procedure for such tests of deposition and whiteness applicable to a firm solid stick used apparatus to apply a deposit from a stick onto a substrate under standardised conditions and then measures the mean level of white deposits using image analysis.

The substrates used were 12×28 cm strips of black cotton fabric. The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to bias the stick against the substrate with a standardised force (500 g load). The apparatus was operated to pass the stick 120 mm laterally across the substrate six times with a final velocity of 140 mm/s. The substrate was carefully removed from the rig and reweighed. The whiteness of the deposit could subsequently be measured as described at (v) below.

(iii) Whiteness of Deposit

The deposits from the at test (ii) above, were assessed for their whiteness after an interval of 24 hours approximately.

This was carried out using a KS Image Analyser fitted with a Sony XC77 monochrome video camera with a Cosmicar 16 mm focal length lens positioned vertically above a black table illuminated from a high angle using fluorescent tubes to remove shadowing. The apparatus was initially calibrated using a reference white card, after the fluorescent tubes had been turned on for long enough to give a steady light output. A cloth with a deposit thereon from the previous test was placed on the table and the camera was used to capture an image. An area of the image of the deposit was selected and analysed using KS400™ image software. This notionally divided the image into a large array of pixels and measured the grey level of each pixel on a scale of 0 (black) to 255 (white). The average of the grey intensity was calculated and can be compared with the background reading for the cloth of 10. This was a starting point to measure the whiteness of the deposit, with higher numbers indicating a whiter deposit. It was assumed that low numbers show a clear deposit allowing the substrate colour to be seen.

(iv) HPLC Method for Purity of Gellant

Purity of the gellant was measured by reverse phase HPLC with UV detection.

A mobile phase was prepared comprising a 300 ml aliquot of deionised water, to which was added a 700 ml aliquot of HPLC grade acetonitrile and 1.0 ml of trifluoroacetic acid (Aldrich™ spectrophotometric grade), all solvents were then mixed thoroughly and degassed. 0.001 g of sample was weighed into a 2 ml HPLC vial and made up to volume with the mobile phase.

The sample was then analysed using a Hewlett Packard 1050 HPLC System™ equipped with a Hypersil ODS 5 μm $C_{18}$, 250×4.6 mm ID column, HP Autosampler™ and UV Diode Array Detector set to 210 nm.

Analysis was carried out under the following conditions:—

| | |
|---|---|
| Isocratic/gradient: | Isocratic |
| Flow rate: | 1.2 ml/minute |
| Run time: | 10 minutes |
| Temperature: | Ambient |
| Injection volume: | 20 μl |

All results are quoted in area percent.

The invention claimed is:

1. A solid cosmetic composition comprising a water-immiscible liquid, a cosmetic active suspended therein and a solidifying amount of a gellant for the water-immiscible liquid, wherein the gellant for the water-immiscible liquid comprises at least 4% by weight of primary and secondary amido gellants, including at least 3% by weight of a primary gellant combination of gellant (i), an N-acyl substituted amino acid amide of formula $A^X$—CO—$R^X$ in which $A^X$ represents the residue of an amino acid amide and $R^X$ represents a branched alkyl group containing from 4 to 12 carbon atoms and gellant (ii), an N-acyl substituted amino acid amide of formula $A^Y$—CO—$R^Y$ in which $A^Y$ represents an amino acid amide and $R^Y$ represents a linear alkyl group containing from 9 to 21 carbon atoms in an effective relative weight ratio as primary gellant and the water-immiscible liquid comprises a water-immiscible monohydric alcohol having a melting point of not higher than 20° C. and a boiling point of higher than 100° C. in a proportion of from 25% to 50% of said water-immiscible liquid.

2. A composition according to claim 1 wherein $A^X$ represents the residue of diamido-substituted glutamic acid or aspartic acid.

3. A composition according to claim 2 wherein $A^x$ represents the residue of diamido-substituted glutamic acid.

4. A composition according to claim 1 wherein each amido substituent in $A^X$ has the formula —CO—NH—$R^Z$ in which $R^Z$ represents an alkyl group containing from 3 to 6 carbon atoms.

5. A composition according to claim 4 wherein $R^z$ represents a linear alkyl group.

6. A composition according to claim 4 wherein $R^Z$ represents butyl.

7. A composition according to claim 1 wherein $R^X$ contains 4 to 8 carbon atoms.

8. A composition according to claim 7 wherein $R^X$ contains 7 or 8 carbon atoms.

9. A composition according to claim 1 wherein $R^X$ contains a single side chain.

10. A composition according to claim 1 wherein —CO—$R^x$ is the residue of 2-ethyl-hexanoic acid.

11. A composition according to claim 1 in which gellant (i) is present in a concentration of from 1.5 to 8% by weight of the composition.

12. A composition according to claim 1 in which gellant (i) is present in a concentration of from 2 to 15% by weight of the water-immiscible oils.

13. A composition according to claim 1 wherein the weight ratio of gellant (i) to gellant (ii) is selected in the range of from 3:1 to 1:3.

14. A composition according to claim 13 wherein the weight ratio of gellant (i) to gellant (ii) is selected in the range of from 2:1 to 1:2.

15. A composition according to claim 1 wherein $R^Y$ represents undecanyl.

16. A composition according to claim 1 wherein $A^Y$ represents the residue of diamido-substituted glutamic acid.

17. A composition according to claim 1 wherein each amido substituent in $A^Y$ has the formula —CO—NH—$R^Z$ in which $R^Z$ represents an alkyl group containing from 3 to 6 carbon atoms.

18. A composition according to claim 1 wherein $R^Z$ represents a linear alkyl group.

19. A composition according to claim 17 wherein $R^Z$ represents butyl.

20. A composition according to claim 1 wherein the proportion of N-acyl amino acid amide gellant (ii) is from 1.5 to 8% by weight of the composition.

21. A composition according to claim 1 wherein the proportion of N-acyl amino acid amide gellant (ii) is from 2 to 15% by weight of the water-immiscible oils.

22. A composition according to claim 1 in which the combined weight of gellants (i) and (ii) forming the primary gellant is from 4.5 to 8% of the composition.

23. A composition according to claim 1 characterised by containing a minor proportion of a secondary gellant selected from one or more amido-containing gellants other than gellants (i) and (ii) or hydroxy-stearic acids.

24. A composition according to claim 22 wherein the total weight of primary and any secondary gellants is from 5 to 10% of the composition.

25. A composition according to claim 1 wherein the alcohol is a branched aliphatic alcohol containing from 12 to 22 carbon atoms.

26. A composition according to claim 1 wherein the proportion of monohydric alcohol of the water-immiscible oils is from 30 to 45% by weight.

27. A composition according to claim 1 wherein the monohydric alcohol is present in a weight ratio to the combined weight of amido gellants of from 3.5:1 to 5:1.

28. A composition according to claim 1 wherein the water-immiscible oil comprises a silicone oil.

29. A composition according to claim 1 wherein the silicone oil is present in a proportion of from 30 to 75% by weight of the water-immiscible carrier oils.

30. A composition according to claim 29 wherein the silicone oil comprises a volatile silicone oil.

31. A composition according to claim 1 wherein the antiperspirant or deodorant active comprises an astringent aluminium and/or zirconium salt.

32. A composition according to claim 1 wherein the aluminium or zirconium salt comprises an aluminium chlorohydrate, an aluminium-zirconium chlorohydrate or an aluminium-zirconium chlorohydrate complex.

33. A composition according to claim 1 wherein the cosmetic active is present in a weight proportion of from 5 to 40% of the composition.

34. A process for the preparation of an antiperspirant or deodorant stick comprising the steps of:
   a. forming a mobile mixture of (i) a liquid phase comprising a water-immiscible oil, (ii) a gellant therefor and (iii) a suspended particulate antiperspirant or deodorant by
   a1. mixing the liquid phase with the gellant,
   a2. heating the liquid phase to a temperature at which the gellant dissolves
   a3. introducing the particulate antiperspirant or deodorant active into the liquid phase either before or after dissolution of the gellant
   b. introducing the mobile mixture into a dispensing container and
   d. cooling or allowing the mobile mixture to cool to a temperature at which it sets wherein the gellant comprises gellant (i) and gellant (ii) as described in claim 1 and from 25% to 50% by weight of the water-immiscible oil is a water-immiscible monohydric alcohol as described in claim 1.

35. A process according to claim 34 wherein at least one of gellants (i) and (ii) are dissolved in a first fraction of the water-immiscible liquid and the antiperspirant or deodorant active is suspended in a second fraction of the water-immiscible liquid and the first fraction is then mixed with the second fraction.

36. A process according to claim 35 wherein the first fraction of liquid comprises said water-immiscible monohydric alcohol.

37. A cosmetic method for inhibiting or controlling perspiration and/or malodour generation comprising applying topically to human skin an effective amount of a cosmetic composition according to claim 1.

* * * * *